United States Patent [19]
Palcisko

[11] Patent Number: 5,708,224
[45] Date of Patent: Jan. 13, 1998

[54] METHOD AND APPARATUS FOR TESTING RESIN TO DETERMINE AGE

[75] Inventor: William M. Palcisko, Durham, N.C.

[73] Assignee: Mitsubishi Semiconductor America, Inc., Durham, N.C.

[21] Appl. No.: 620,228

[22] Filed: Mar. 22, 1996

[51] Int. Cl.$^6$ .................. G01N 3/08; G01N 33/44
[52] U.S. Cl. .................. 73/866; 73/788; 73/790; 73/818
[58] Field of Search .................. 73/12.01, 78, 82, 73/760, 788, 790, 818, 866

[56] References Cited

U.S. PATENT DOCUMENTS

| | | | |
|---|---|---|---|
| 2,259,491 | 10/1941 | Roller | 73/790 |
| 2,892,342 | 6/1959 | Goss et al. | 73/82 |
| 3,693,421 | 9/1972 | Karper | 73/12.01 X |
| 4,111,039 | 9/1978 | Yamawaki et al. | 73/82 X |
| 4,140,008 | 2/1979 | Golembeck et al. | 73/78 |
| 4,238,952 | 12/1980 | Koopmann et al. | 73/822 |
| 4,565,089 | 1/1986 | Arciszewski et al. | 73/82 |
| 4,616,508 | 10/1986 | Alfred. | |
| 4,914,602 | 4/1990 | Abe et al.. | |
| 4,934,199 | 6/1990 | Avila et al.. | |
| 4,957,012 | 9/1990 | Cuddihy et al.. | |
| 5,092,175 | 3/1992 | Winckler et al.. | |
| 5,142,911 | 9/1992 | Mathys. | |
| 5,245,861 | 9/1993 | Limper et al.. | |
| 5,373,750 | 12/1994 | Butler et al.. | |
| 5,396,804 | 3/1995 | Moet et al.. | |
| 5,438,863 | 8/1995 | Johnson | 73/54.02 |

FOREIGN PATENT DOCUMENTS

| | | | |
|---|---|---|---|
| 13133 | 1/1986 | Japan | 73/818 |
| 01-035239 | 2/1989 | Japan. | |
| 03-028737 | 2/1991 | Japan. | |
| 04-343485 | 11/1992 | Japan. | |
| 05-010865 | 1/1993 | Japan. | |

*Primary Examiner*—Hezron E. Williams
*Assistant Examiner*—Daniel S. Larkin
*Attorney, Agent, or Firm*—Lowe, Price, LeBlanc & Becker

[57] ABSTRACT

A method and apparatus for testing a pellet of resin to determine its age comprises preheating the pellet and subjecting it to a deformation force in a measurement fixture for a predetermined time period. At the expiration of the predetermined time period, the deformation of the pellet is measured and compared to an expected deformation of the resin as a function of the resin age to determine the age of the pellet.

29 Claims, 2 Drawing Sheets

METHOD AND APPARATUS FOR TESTING RESIN TO DETERMINE AGE

TECHNICAL FIELD

The present invention relates to testing the age of a material, and more particularly, to a method and apparatus for testing a deformable material, such as a resin, to determine its age.

BACKGROUND ART

In semiconductor applications, various components of the semiconductors are made from semiconductor molding compounds, such as epoxy resins. Epoxy resins exhibit excellent adhesion properties and good mechanical, humidity and chemical resistance properties. However, as the resins age, these properties deteriorate so that the resins no longer perform as designed. Usually, epoxy resins are labeled in some way to indicate an expiration date. After the expiration date, the resins are discarded to avoid possible failure.

However, aging of a resin is not uniform. The life of a resin may vary depending on, for instance, the environmental conditions to which the resin is exposed. Illustratively, a resin exposed to elevated temperatures may be expected to age at a faster rate than a resin at room temperature. Similarly, a refrigerated resin may be expected to age at a slower rate than a resin stored at room temperature. These rates, however, are not uniform, and hence it is difficult to evaluate the useful age of resin solely based upon the labeled expiration date of the resin.

Accordingly, it would be desirable to test a pellet of resin to determine its age.

Also, it would be desirable to test a pellet or group of pellets of resin to determine age as a function of an easily measurable physical characteristic of the resin. Such a test should be repeatable among samples and over time.

DISCLOSURE OF THE INVENTION

Accordingly, one advantage of the present invention is in providing a method and apparatus for determining the expected resistance to deformation of a preheated resin as a function of the age of the resin to facilitate determination of the age of a resin sample.

Another advantage of the present invention is in providing a method and apparatus for determining the age of a pellet of resin.

A further advantage of the present invention is in providing a method and apparatus for determining the age of a pellet of resin which is easily repeatable among samples and over time.

Yet another advantage of the present inventor is in providing a method and apparatus for determining age as a function of an easily measurable physical characteristic of the resin.

These and other advantages of the invention are achieved, at least in part, by providing an apparatus for testing a pellet of resin to determine the age of the pellet, comprising a source of heat for preheating the pellet and a fixture. The fixture includes a base supporting the pellet, a mass selectively positioned so as to exert a deformation force on the pellet, and a scale for measuring deformation of the pellet in response to the deformation force.

In accordance with one aspect of the invention, a timer activates the scale at the expiration of a predetermined time period.

In accordance with another aspect of the invention, the mass is positioned vertically over the pellet, and the scale measures the vertical deformation of the pellet.

In accordance with a further aspect of the invention, the fixture includes a support, a movable plate displaceable along the support on which the mass is positioned, and a release. Upon actuation of the release, a bottom surface of the movable plate contacts and exerts the deformation force on the pellet. Preferably, the scale is electronic, is mounted to the movable plate and measures the displacement of the movable plate.

The present invention also provides a method of determining the age of a pellet of resin. According to the method, the pellet of resin is treated and subjected to a deformation force for a predetermined time period. At the expiration of the predetermined time period, deformation of the pellet is measured and compared to a predetermined expected deformation of the resin as a function of the age of the resin to determine the age of the pellet.

In accordance with an aspect of the invention, the the predetermined expected deformation as a function of age is a graphical representation formulated by measuring a sample of pellets at various times over the life of the sample of pellets.

In accordance with another aspect of the invention, the predetermined expected deformation as a function of age is a graphical representation formulated by measuring a sample of pellets of varying known ages.

In accordance with yet another aspect of the invention, the step of treating the pellet comprises preheating the pellet, preferably to a temperature in the range of approximately 70° to approximately 90° C.

In accordance with a further aspect of the invention, the treated pellet is subjected to deformation load in a direction, and the step of measuring the deformation is accomplished by measuring displacement of the load at the expiration of the predetermined time period.

Preferably, an electronic scale is used to measure the displacement.

Also preferably, the predetermined time period is in the range of approximately 10 seconds to approximately 30 seconds.

The invention is also directed to a method of determining the deformation properties of a resin as a function of age. A pellet of the resin of a known age is treated, preferably by preheating, and subjected to a deformation force for a predetermined time period. At the expiration of the predetermined time period, the deformation of the pellet is measured and recorded. These steps are repeated for pellets of varying ages to determine the deformation properties of the resin as a function of age.

Preferably, the deformation of each pellet is graphed as a function of the age of the pellet to obtain a graphical representation of the expected deformation of the resin as a function of age.

According to another aspect of the invention, the steps are repeated for a pellet of unknown age, and the measured deformation of the pellet of unknown age is compared to the determined deformation properties of the resin as a function of age to determine the age of the pellet of unknown age.

The invention is also directed to another method of determining the deformation properties of a resin as a function of age. A pellet of the resin of a known age is treated, preferably by preheating, and subjected to a deformation force for a predetermined time period. At the expiration of the predetermined time period, the deformation of the pellet is measured and recorded. These steps are repeated for the pellet at various times over the life of the pellet to determine the deformation properties of the resin as a function of age.

Preferably, the deformation of the pellet is graphed as a function of the age of the pellet to obtain a graphical representation of the expected deformation of the resin as a function of age.

According to another aspect of the invention, the steps are repeated for a pellet of unknown age, and the measured deformation of the pellet of unknown age is compared to the determined deformation properties of the resin as a function of age to determine the age of the pellet of unknown age.

BEST MODE FOR CARRYING OUT THE INVENTION

Figure 1:
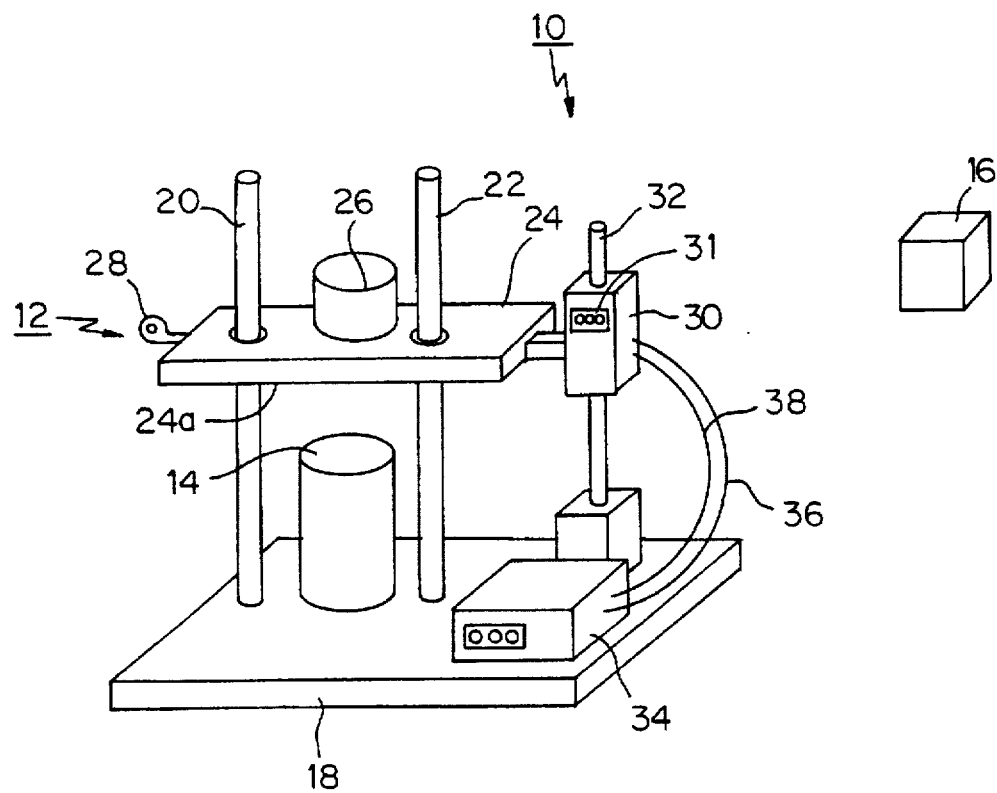
FIG. 1 is a perspective view of the apparatus of the present invention.

Referring to FIG. 1, an apparatus 10 of the present invention is depicted and includes a fixture 12 with a pellet 14 placed thereon and a heat source 16. Heat source 16 may be any conventional heat source, such as a microwave oven, a convection oven, a conventional oven or a burner. Heat source 16 may be located adjacent fixture 12 or at a remote site, as long as the pellet remains at the desired temperature during transport from the remote site to fixture 12. Optionally, heat source 16 may be integral with fixture 12.

Apparatus 10 generally includes a base 18 supporting pellet 14 and a pair of vertical supports 20, 22 along which a movable plate 24 is displaced. A mass 26 is positioned on movable plate 24. Mass 26 is sufficient to cause deformation of the resin when preheated. The mass will vary depending on the type of resin tested and the type of test results desired. For instance, a heavier mass will result in more rapid deformation. It is preferred that mass 26 be standardized to enable fixture 12 to be massed produced. Mass 26 may be merely placed on movable plate 24 or may be secured to movable plate 24, such as by welding. Optionally, mass 26 may be replaced with any conventional mechanical force sufficient to provide a certain amount of known force. For instance, the mechanical force may be provided by a hydraulic piston, levers, or pressurized air.

Movable plate 24 is held in the position depicted in FIG. 1 by a release 28. While release 28 is depicted in FIG. 1 as a quick release pin, any suitable release mechanism may be utilized.

A scale 30 is mounted to movable plate 24 so as to move vertically therewith. Preferably, scale 30 is supported by and movable along a vertical support 32. Scale 30 measures the vertical displacement of movable plate 24, as will be hereinafter described. Scale 30 may be of any conventional type, and is preferably an electronic scale including a linear displacement indicator 31 for ease of reading.

A timer 34 is operatively connected to scale 30 by any conventional means, such as wires 36, 38. Generally, the timer 34 is preset for a predetermined time period, and at the expiration of the predetermined time period, the timer will cause the electronic scale 30 to maintain the value displayed by displacement indicator 31 at that time.

Figure 2:
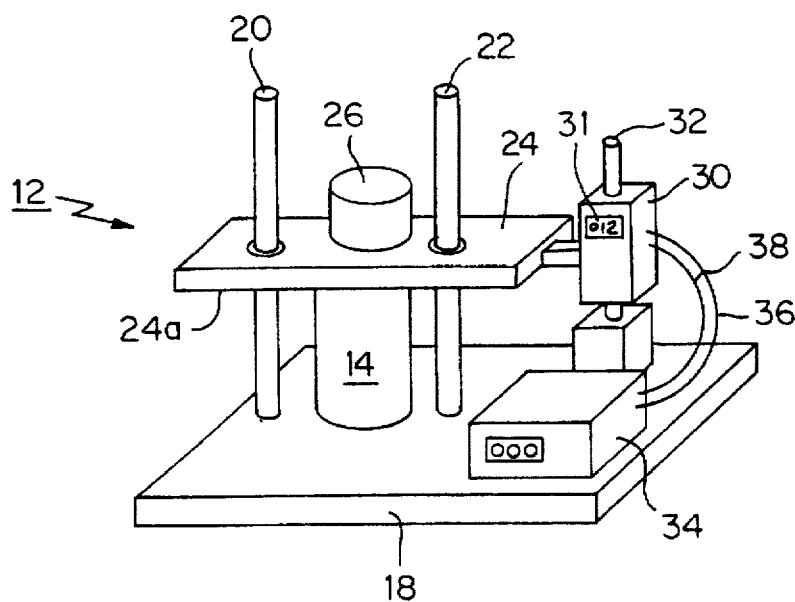
FIG. 2 is a perspective view of the apparatus of FIG. 1 upon initial application of a deformation load to an epoxy pellet.

The operation of the apparatus 10 will now be described, with reference to FIGS. 1 through 3. The pellet 14 is first preheated by the heat source 16 to a predetermined temperature and placed into the fixture 12, depicted in FIG. 1 in its preliminary position. Preheating of the pellet is required as a pellet of room temperature will not deform under the force of mass 26. Alternatively, the pellet may be, for instance, chemically treated if it would result in deformation of the pellet under load. The scale 30 is originated so as to display a value of 000 on displacement indicator 31.

The release 28 is then actuated, for instance, by removing the quick release pin, as depicted in FIG. 1, from fixture 12. Upon actuation of the release 28, the movable plate 24 drops so that a bottom surface 24a thereof contacts pellet 14. This position is depicted in FIG. 2. At this position, the scale 30 displays a value on the displacement indicator 31 equal to the distance between the preliminary position of movable plate 24 of FIG. 1 and the position depicted in FIG. 2. For instance, as shown in the drawings, the displacement indicator 31 displays a value of 012. As the bottom surface 24a of movable plate 24 contacts pellet 14, and thus exerts a force on pellet 14, the timer is activated to begin counting the predetermined time period.

Figure 3:
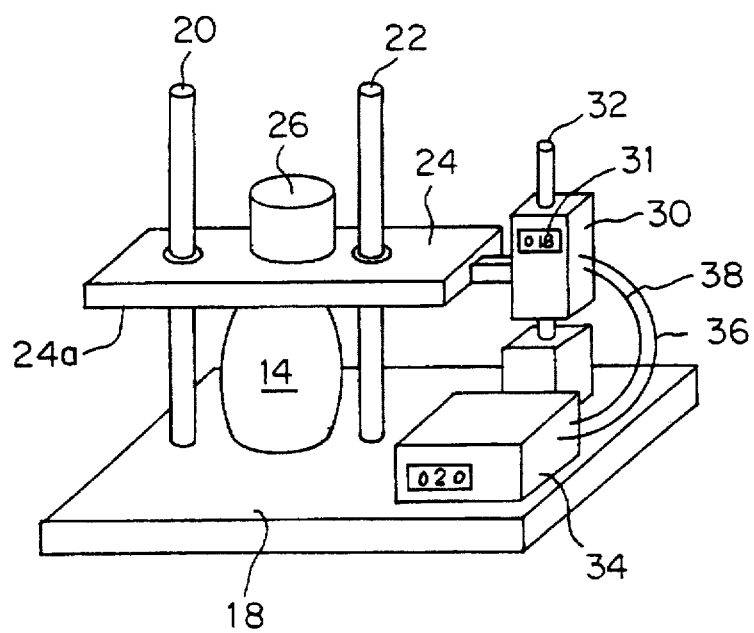
FIG. 3 is a perspective view of the apparatus of FIGS. 1 and 2 depicting the pellet after the expiration of a predetermined time period.

Referring now to FIG. 3, the fixture is depicted at the expiration of the predetermined time period. The pellet 14 is seen to have undergone some deformation, in this case, the pellet has bellowed outwardly. As a result of the deformation, the position of movable plate 24 is lower than that depicted in FIG. 2. Accordingly, the displacement indicator 31 displays a higher value than that displaced in FIG. 2. For instance, the displacement indicator 31 displays a value of 018. This value is maintained on the display once the timer times out.

There are a number of uses for the apparatus and method disclosed herein. Primarily, the method is useful in determining the age of a particular pellet or group of pellets taken from a lot of resin currently in use in the production line. To determine the age of a particular pellet or group of pellets, it is first necessary to determine the expected deformation of the resin as a function of the age of the resin. The deformation of the particular pellet or group of pellets is then compared to the expected deformation as a function of age to determine the age of the particular pellet or group of pellets. The expected deformation as a function of age may be determined by either testing a group of pellets of the same age at various times over the life of the pellets, or by testing a group of pellets of varying known ages. It is preferred to represent the expected deformation as a function of age graphically, as depicted in FIG. 4.

Figure 4:
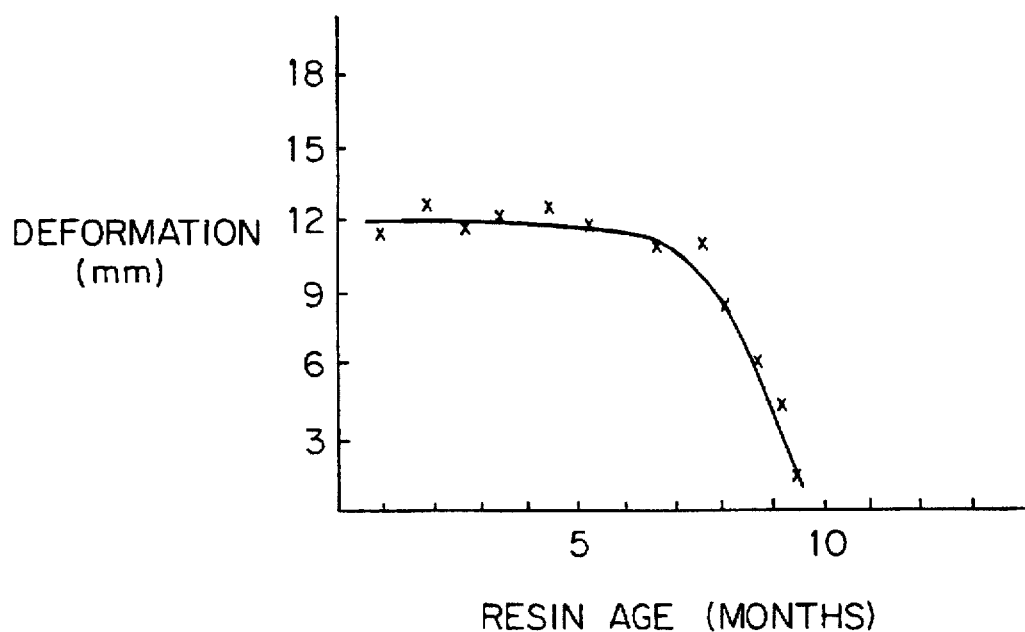
FIG. 4 is a sample graphical representation of the deformation of an epoxy resin as a function of the age of the resin.

In the example of FIG. 4, the graphical representation of the expected deformation of an epoxy resin as a function of age was determined by testing a group of pellets of varying known ages. Each pellet was first preheated to a temperature in the range of approximately 70° C. to approximately 90° C. The preheated pellet was then placed in the fixture 12 with mass 26 in the range of approximately 10–15 lbs. Upon actuation of the release 28, the mass 26 exerted a deformation force on the pellet for a predetermined time period in the range of approximately 10 seconds to approximately 30 seconds. At the expiration of that time period, the linear deformation indicator 31 of scale 30 is read and recorded. The recorded deformation of the group of pellets are then plotted as a function of the age of the pellet, resulting in the graphical representation of FIG. 4.

As can be observed from FIG. 4, a resin typically stiffens, i.e., provides a greater resistance to deformation, as it ages. For instance, the resin tested at four months of age deforms approximately 13 mm, while the resin tested at nine months of age deforms only approximately 6 mm. The deformation of a specimen pulled from the production line and tested by the apparatus of the present invention and according to the method of the present invention is easily compared to the graph of FIG. 4 to determine the approximate age of the resin. Once the approximate age of the resin is known, a decision can be made as to whether the resin is of an appropriate age for the intended use.

Although the invention has been described for use with epoxy resin, the method and apparatus of the present invention is equally applicable for use with any thermoset plastic or semiconductor molding compound which deforms under heat or other treatment.

It will become apparent to one of ordinary skill in the art that various adaptations to the invention described herein are possible, without departing from the scope of the invention. For instance, the deformation force may be applied in any arbitrary direction. The fixture may also be modified to include a heat chamber for preheating the pellet. Another alternative is to insert a temperature sensor into the pellet to indicate when a desired temperature has been reached. Yet another alternative is to treat the pellet, chemically, for instance, until the pellet reaches a state capable of deformation. Furthermore, the fixture may be automated, i.e., by connecting the fixture to a microprocessor to control the actuation of the deformation force, or to measure, record and/or analyze the recorded measurements. It may further be desirable to provide software to predict the outcome of a test upon input of the test variables, wherein the test result is automatically compared to the predicted outcome. It will be understood that these and other variations are within the scope of the present invention.

In summary, the results and advantages of the testing method and apparatus of the present invention can now be more fully appreciated. The method and apparatus of the present invention provides a simple testing procedure by which the expected deformation of a resin as a function of age can be determined. Additionally, the method and apparatus of the present invention permits the testing of a pellet of resin to determine the deformation of the pellet under a deformation load, and comparison of the resulting deformation to a predetermined expected deformation of the resin as a function of the age of the resin leads to a determination of the age of the pellet.

In this disclosure, there is shown and described only the preferred embodiment of the invention, but, as aforementioned, it is to be understood that the invention is capable of use in various other combinations and environments and is capable of changes or modifications within the scope of the inventive concept as expressed herein.

What is claimed is:

1. A method of determining the age of a pellet of resin comprising the steps of:
   (a) treating the pellet of resin;
   (b) subjecting the treated pellet to a deformation force for a predetermined time period;
   (c) measuring deformation of the pellet at the expiration of the predetermined time period; and
   (d) comparing the measured deformation of the pellet to a predetermined expected deformation of the resin as a function of the age of the resin to determine the age of the pellet.

2. The method of claim 1, wherein the predetermined expected deformation as a function of age is a graphical representation formulated by measuring deformation of a pellet at various times over the life thereof.

3. The method of claim 1, wherein the predetermined expected deformation as a function of age is a graphical representation formulated by measuring pellets at various times over the life of the pellets.

4. The method of claim 1, wherein the predetermined expected deformation as a function of age is a graphical representation formulated by measuring a sample of pellets of varying known ages.

5. The method of claim 1, wherein the step of treating the pellet comprises preheating the pellet.

6. The method of claim 5, wherein the pellet is preheated to a temperature in the range of approximately 70° C. to approximately 90° C.

7. The method of claim 1, wherein the treated pellet is subjected to deformation load in a direction, and the step of measuring the deformation is accomplished by measuring displacement of the load at the expiration of the predetermined time period.

8. The method of claim 7, wherein the displacement is measured by an electronic scale.

9. The method of claim 1, wherein the predetermined time period is in the range of approximately 10 seconds to approximately 30 seconds.

10. The method of claim 1, wherein after the step of treating the pellet, the method comprises the step of:
   placing the treated pellet into a fixture;
   wherein steps (b) and (c) occur while the pellet is in the fixture.

11. The method of claim 1, wherein prior to treating the pellet, the method comprises the step of:
   placing the pellet into a fixture;
   wherein steps (a), (b) and (c) occur while the pellet is in the fixture.

12. An apparatus for testing a pellet of resin to determine its age, comprising:
   a source of heat for preheating the pellet; and
   a fixture including a base on which the entire resin pellet is supported, a mass selectively positioned so as to exert a deformation force on the pellet, and a scale for measuring pellet deformation in response to the deformation force.

13. The apparatus of claim 12, further comprising a timer activating the scale at the expiration of a predetermined time period.

14. The apparatus of claim 12, wherein the mass is positioned vertically over the pellet, and wherein the scale measures the vertical deformation of the pellet.

15. The apparatus of claim 12, wherein the fixture further includes a support and a movable plate displaceable along the support on which the mass is positioned.

16. The apparatus of claim 15, wherein the fixture further includes a release, wherein upon actuation of the release, a bottom surface of the movable plate contacts and exerts the deformation force on the pellet.

17. The apparatus of claim 15, wherein the scale is mounted to the movable plate and measures displacement of the movable plate.

18. The apparatus of claim 12, wherein the scale is electronic.

19. A method of determining the deformation properties of a resin as a function of age, comprising the steps of:
   (a) treating a pellet of the resin of a known age;

(b) subjecting the treated pellet to a deformation force for a predetermined time period;

(c) measuring deformation of the pellet at the expiration of the predetermined time period;

(d) recording the deformation of the pellet as a function of the known age; and (e) repeating steps (a) through (d) for pellets of varying ages to determine the deformation properties of the resin as a function of age.

20. The method of claim 19, further comprising the step of:

(f) graphing the deformation of each pellet as a function of the age of the pellet to obtain a graphical representation of the expected deformation of the resin as a function of age.

21. The method of claim 19, further comprising the steps of:

(f) repeating steps (a) through (d) for a pellet of unknown age; and (g) comparing the measured deformation of the pellet of unknown age to the determined deformation properties of the resin as a function of age to determine the age of the pellet of unknown age.

22. The method of claim 20, further comprising the steps of:

(g) repeating steps (a) through (d) for a pellet of unknown age; and (h) comparing the measured deformation of the pellet of unknown age to the graphical representation of the expected deformation of the resin as a function of the age of the resin to determine the age of the pellet of unknown age.

23. The method of claim 19, wherein the step of treating the pellet comprises preheating the pellet.

24. A method of determining the deformation properties of a resin as a function of age, comprising the steps of:

(a) treating a pellet of the resin of a known age;

(b) subjecting the treated pellet to a deformation force for a predetermined time period;

(c) measuring deformation of the pellet at the expiration of the predetermined time period;

(d) recording the deformation of the pellet as a function of the known age; and (e) repeating steps (a) through (d) for the pellet at various times over the life of the pellet to determine the deformation properties of the resin as a function of age.

25. The method of claim 24, further comprising the step of:

(f) graphing the deformation of the pellet as a function of the age of the pellet to obtain a graphical representation of the expected deformation of the resin as a function of age.

26. The method of claim 24, further comprising the steps of:

(f) repeating steps (a) through (d) for a pellet of unknown age; and (h) comparing the measured deformation of the pellet of unknown age to the determined deformation properties of the resin as a function of age to determine the age of the pellet of unknown age.

27. The method of claim 25, further comprising the steps of:

(g) repeating steps (a) through (d) for a pellet of unknown age; and (h) comparing the measured deformation of the pellet of unknown age to the graphical representation of the expected deformation of the resin as a function of the age of the resin to determine the age of the pellet of unknown age.

28. The method of claim 20, further comprising the step of:

(f) repeating steps (a) through (e) for a plurality of pellets.

29. The method of claim 28, wherein the step of treating the pellet comprises preheating the pellet.

* * * * *